United States Patent [19]

Shaw

[11] Patent Number: 5,312,739
[45] Date of Patent: May 17, 1994

[54] PRODUCTION OF HIGH-MALTOSE SYRUP AND HIGH-PROTEIN BYPRODUCT FROM MATERIALS THAT CONTAIN STARCH AND PROTEIN BY ENZYMATIC PROCESS

[75] Inventor: Jei-Fu Shaw, Nankang, Taiwan
[73] Assignee: National Science Council, Taiwan
[21] Appl. No.: 889,809
[22] Filed: May 28, 1992
[51] Int. Cl.$^5$ .................. C12P 19/12; C12P 21/06; C12P 19/22
[52] U.S. Cl. .................. 435/95; 435/68.1; 435/96; 435/98; 435/99; 435/100; 435/101; 435/272; 536/124
[58] Field of Search .................. 435/100, 101, 99, 98, 435/96, 68.1, 95, 272; 536/124

[56] References Cited

U.S. PATENT DOCUMENTS

| | | | |
|---|---|---|---|
| 3,996,107 | 12/1976 | Martensson | 435/98 |
| 4,282,319 | 8/1981 | Conrad | 435/68.1 |
| 4,448,790 | 5/1984 | Sarkki et al. | 435/99 |
| 4,560,651 | 12/1985 | Nielsen et al. | 435/95 |
| 4,814,267 | 3/1989 | Zeikus et al. | 435/95 |
| 4,970,158 | 11/1990 | Outtrup et al. | 435/95 |
| 5,013,561 | 5/1991 | Goering et al. | 435/99 |
| 5,141,859 | 8/1992 | Niimi et al. | 435/100 |
| 5,188,956 | 2/1993 | Nanmori et al. | 435/95 |

OTHER PUBLICATIONS

Tu et al., *Chemical Abstracts*, vol. 110(1), Jan. 2, 1989, #6651z.
Niimi et al., *Chemical Abstracts*, vol. 113(17), Oct. 22, 1990, #150889r.
Niimi et al., *Chemical Abstracts*, vol. 114(1), Jan. 7, 1991, #4883k.
CA 117(15) 149681q Shaw et al Jul. 1992 7 Abstract Biosci, Biotech, Biochem 56(7) 1071–3 Jul. 1992.
Bienvenido O. Juliano, Rice Starch: Production, Properties and Uses, Chapter XVI, pp. 506–529–1984.
B. M. Kennedy, et al., Cereal Chemistry, vol. 51, Jul.–Aug. 1974, No. 4, pp. 435–449.
D. F. Houston, "High-Protein Flour Can Be Made From All Types Of Milled Rice", The Rice Journal, Aug., 1967, pp. 12–19.

Primary Examiner—Herbert J. Lilling
Attorney, Agent, or Firm—Winstead Sechrest & Minick

[57] ABSTRACT

An enzymatic process is developed to produce high-maltose syrup and high-protein byproduct simultaneously from materials that contain starch and protein. In the process, the slurry of milled starting material is first liquefied with α-amylase and then centrifuged. The precipitated fraction is recovered as high-protein flour. The supernatant fraction was then saccharified with β-amylase and debranching enzyme (isoamylase or pullulanase) simultaneously to produce high-maltose syrup at various conditions. The yield of high-maltose syrup is affected by temperature, pH, DE values of liquefied starch, different enzyme combinations and varieties of starting materials.

7 Claims, No Drawings

PRODUCTION OF HIGH-MALTOSE SYRUP AND HIGH-PROTEIN BYPRODUCT FROM MATERIALS THAT CONTAIN STARCH AND PROTEIN BY ENZYMATIC PROCESS

BACKGROUND OF THE PRESENT INVENTION

The present invention relates to an enzymatic process for the simultaneous production of high-maltose syrup and high-protein byproduct from materials that contain starch and protein.

High-maltose syrup has mild sweetness, low viscosity in solution, low hygroscopicity and good heat stability. Therefore, it is well suited for numerous applications in food industry such as high quality products of candy, ice cream, etc. It is also suitable for diabetics (U.S. Pat. No. 3,793,461, 1974). The conventional process for the production of high-maltose syrup uses purified starch as starting material. High-protein flour has high nutritional value and is useful for the production of pudding, gruel, instant milk and baby food, etc. (D. F. Houston, Rice J., 70, 12, 1967; B. M. Kennedy et. al., Cereal Chem., 51, 435, 1974).

The traditional process for the separation of starch from protein is tedious and costly (B. O. Juliano, "Starch: Chemistry and Technology", 2nd ed.; Whister, R. L., Bemiller, J. N. and Paschall, E. F., eds., Academic Press New York, pp 507–528, 1984). Furthermore, the use of unnatural chemicals such as sodium hydroxide, acid and surfactants are undesirable for food use.

SUMMARY OF THE PRESENT INVENTION

It is an objective of the present invention to provide an enzymatic process to produce high-maltose syrup and high-protein flour simultaneously from materials that contain starch and protein, also to provide a natural process that no unnatural chemicals are used in the process.

In accordance with the present invention, an enzymatic process is developed to produce high-maltose syrup and high-protein flour simultaneously from materials that contain starch and protein. Thermostable $\alpha$-amylase is used to digest the starch into soluble oligosaccharide in the autoclave. The heat-coagulated protein is easily separated from the soluble starch hydrolysate and recovered as high-protein flour. The starch hydrolysate is further treated with debranching enzyme (such as isoamylase and pullulanase) and $\beta$-amylase to produce high-maltose syrup. The enzymatic process of the present invention is natural and therefore desirable for various uses such as food or feed.

DETAILED DESCRIPTION OF THE PRESENT INVENTION

The objectives, features, and advantages of the present invention can be better understood from the following examples.

EXAMPLE 1

Milled rice (rice flour) of various cultivars were obtained from Taichung Agricultural Experimental Station (Changhua, Taiwan, Republic of China), i.e., Tainung 70, Taichung Glutinous 70, Taichung Sen Glutinous, and Taichung Native 1.

A 10% slurry of rice flour (>100 mesh) of various cultivars in deionized water was mixed thoroughly with various amount of thermostable *B. licheniformis* $\alpha$-amylase (Type XIIA, from Sigma Chemical Co., St. Louis, Mo.) in an autoclave, and the starch in the rice flour was liquefied before the rising temperature reached the point of $\alpha$-amylase denaturation. The final condition of the autoclave process was 128° C. and 1.5 atm. All the proteins in the rice flour were essentially heat-coagulated in this liquefied process and were easily separated from the soluble starch hydrolysate by centrifugation at 10,000 g for 30 minutes. The precipitated fraction was dried and recovered as high-protein rice flour. The supernatant (mostly oligosaccharide mixtures $\geq$DP 7) was further treated with various combinations of $\beta$-amylase and debranching enzymes to produce the high maltose syrup.

All the samples of $\alpha$-amylase-liquefied rice starch hydrolysate (10% DS) were saccharified with 300 U g$^{-1}$ DS (dry solid) of *Bacillus cereus* $\beta$-amylase (obtained from Amano Pharmaceutical Co., Nagoya, Japan) and 5 U g$^{-1}$ DS of pullulanase (obtained from Sigma Chemical Co., St. Louis, Mo.) together at 50° C. and pH 5.0 for 60 h. In addition, Taichung Native 1 rice starch hydrolysate with DE 14 and 4 were obtained from liquefaction with 56.64 and 14.16 U g$^{-1}$ DS $\alpha$-amylase, respectively, and all other samples resulted from the liquefaction with 28.32 U g$^{-1}$ DS $\alpha$-amylase. As a result, the yields and composition of high-protein rice flour and high-maltose syrup from several rice cultivars are shown in Table I.

The concentrations of glucose, maltose and maltotriose in the high maltose syrup were measured by high-performance liquid chromatography (a JASCO TRIROTAR SR-2 HPLC System equipped with JASCO 830 RI detector) with BIORAD HPX-87C column (300×7.8 mm). The mobile phase was distilled water at a flow rate 0.6 ml min$^{-1}$ and column temperature 80° C. The retention times for glucose, maltose, maltotriose and maltotetraose were 10.38, 8.66, 7.89 and 7.46 min, respectively. In addition, the compositions of high-protein rice flour were analyzed according to A.O.A.C. methods ("Official Methods of Analysis", 14 ed. 1984, Association of Official Analytical Chemists, Washington, D.C.). Reducing sugars were determined by dinitrosalicylic acid method (G. L. Miller, Anal. Chem., 31, 426–430, 1959). Crude protein was determined by Kjeldahl Method with Kjeltec Auto 1030 Analyzer (Tecator, Sweden).

As shown in Table I, the protein content of rice flour increased from 9.2–10.9 % in the starting material to 25–53 % in the high protein rice flour ($\alpha$-amylase digested product). In contrast, the starch content was reduced from 77–84% to 16–42%. The different composition of the high-protein rice flour from different rice cultivars are presumably due to the difference in their structures of protein and starch, which affected the $\alpha$-amylase digestion. The starch contents of rice cultivars Tainung 70, Taichung Glutinous 70, Taichung Sen Glutinous and Taichung Native 1 are 76.85%, 78.52%, 79.26% and 83.50%, respectively. The amylose contents for those four cultivars are 19 %, 8 %, 8% and 28%, respectively. As shown in Table I, the high-amylose cultivars apparently produced maltose syrups containing higher maltose.

The maltose level of syrup wa also greatly affected by the dextrose equivalent value (DE) of starting rice starch hydrolysate. The maltose content in the syrup produced from rice starch hydrolysate (Taichung Native 1, 10% DS, pH 4) with DE values 4,9 and 14 were 84.3%, 80.2% and 76.4%, respectively, using 300 U $g^{-1}$ DS of *Bacillus cereus* β-amylase and 5 U $g^{-1}$ DS of pullulanase together at 50° C. To produce syrups containing higher maltose, the starting material should have a DE as low as possible since this would prevent the formation of glucose polymers with uneven chain length and lower the formation of maltotriose after β-amylase hydrolysis.

The low DE starch hydrolysate can be obtained by lowering the amount of added α-amylase in the liquefaction process. However, low DE starch is more viscous and difficult to separate from protein fraction, which resulted in higher yield but lower protein content in the high-protein flour. For example, Taichung Native 1 rice flour liquefied with 14.16, 28.32 and 56.64 U $g^{-1}$ DS α-amylase produced-thinned starch with DE values 4, 9 and 14, respectively and the protein contents in the high-protein rice flours were 25.2, 28.5 and 37.7%, respectively (Table I).

EXAMPLE 2

For the same α-amylase-thinned starch of Taichung Native 1 in Example 1, both isoamylase and pullulanase were used in combination with *B. Cereus* β-amylase to produce high-maltose syrup.

As shown in Table II, the highest maltose level (83.2%) was obtained using both debranching enzymes together. However, pullulanase alone was better than isoamylase alone. Five units of pullulanase was more effective than 2000 units of isoamylase in high-maltose production possibly due to the instability of isoamylase in the saccharification condition.

For the isoamylase-Bacillus β-amylase system, the maltose contents in the syrups produced from α-amylase-thinned rice flour starch (Taichung Native 1, 10% DS, DE 14, pH 5.0) at 40°, 50° and 60° C. were 72, 72 and 61% respectively. In contrast, the maltose contents in the syrup produced from the same starch hydrolysate at pH 4 and temperature 40°, 50° and 60° C. were 74, 72 and 63%, respectively; those at pH 6 and temperature 40°, 50° and 60° C. were 72, 66 and 58%, respectively. Therefore, the best condition for the production of maltose using isoamylase-Bacillus β-amylase system is pH 4 and 40° C. This is consistent with our previous observation that isoamylase is most stable at pH 4 and the stability of isoamylase is a limiting factor in this enzymatic system for high-maltose syrup production. For the pullulanase Bacillus β-amylase system, the best condition is pH 4 and 50° C. Without debranching enzyme, Bacillus β-amylase alone can only produce low level of maltose (58%) in the same condition.

EXAMPLE 3

For the same α-amylase-thinned rice flour (10% DS, DE 9) obtained from Example 1, sweet potato β-amylase (85 units/mg, a 20–70% ammonium sulfate fraction of the pressed sweet potato juice from Tainung 5 cultivar) or *B. Cereus* β-amylase were used in combination with pullulanase to produce high-maltose syrup.

As shown in Table III, sweet potato β-amylase in combination with pullulanase was more effective in high-maltose syrup production than *B. cereus* β-amylase in 12 h saccharification at pH 5 or 6, but it was very poor at pH 4. For longer saccharification time (60 h), the maltose level produced by sweet potato β-amylase was decreased possibly due to the formation of reversion product.

EXAMPLE 4

During the rainy season, rice will germinate quickly, often causing a loss of that rice as a food crop to farmers. Therefore, the present process is used for the production of high-maltose syrup and high protein feed from the agrowaste (germinated rice).

Rice seed of Tainung 70 was sterilized by 0.3% $H_2O_2$, and then was soaked in water for three days. After that, the germinated rice was placed in an incubator for germinating at 30° C. for different length of time (see Table IV). As described in Example 1, milled germinated rice was treated with α-amylase to obtain a starch hydrolysate and a precipitated fraction. Then, the starch hydrolysate (the supernatant) was added with 5 U $g^{-1}$ DS of pullulanase and 300 U $g^{-1}$ of *Bacillus cereus* β-amylase at 50° C., pH 5.0. After a total reaction time of 60 hours, a 62.8–78.4% maltose containing syrup was obtained and the yield was 0.6–0.72 g syrup/ g dry rice. As shown in Table IV, the longer germinating time (the longer shoot) will produce the lower maltose-level syrup or lower yield of syrup.

EXAMPLE 5

Fresh sweet potato (Tainung 57) was pressed, wherein about 45% of 1 kg of sweet potato can be pressed into juice, and 560,000 units of sweet potato β-amylase will be obtained from a 20–70% ammonium sulfate fraction of the pressed sweet potato juice.

The leftover sweet potato (after pressing) was liquefied with α-amylase as in Example 1, then the supernatant was saccharified with 5 $Ug^{-1}$ DS of pullulanase and 300 $Ug^{-1}$ DS of sweet potato β-amylase for 12 hours at 60° C., pH 5.0. As a result, the yield is 0.8 g of syrup/ g of dry sweet potato, and the maltose content in the high maltose syrup is 81.5 %. In addition, the precipitated fraction was recovered as high-protein sweet potato flour, wherein the protein content was increased from 4.2% in the starting sweet potato to 20.5% in the flour, and the yield is 0.2 g high-protein flour/ g dry sweet potato.

Furthermore, the sweet potatoes contain a trypsin inhibitor which is unfavorable to digestion. However, the inhibitor will be denatured after the high temperature treatment (128° C., 1.5 atm), therefore, a high nutritious food may be produced from the high-protein sweet potato flour. As a result, high-maltose syrup, high-protein flour and sweet potato β-amylase were produced simultaneously from the sweet potatoes in this example.

In conclusion, the enzymatic process for the simultaneous production of high maltose syrup and high-protein flour is an efficient and natural process which is applicable to other starch and protein containing crops such as corn, barley, wheat and legumes. To produce syrups containing higher maltose, cultivars of higher amylose to amylopectin ratio and lower DE starch hydrolysate should be used for saccharification. Thermal stable amylases and debranching enzyme with proper pH adjustment and temperature control are also desirable.

TABLE I

The Composition of High-Maltose Syrup and High-Protein Rice Flour Produced from various Rice Cultivars.

| Rice cultivars | DE | High-maltose syrup Yield (g syrup/g rice) | Composition (%) Maltotriose | Maltose | Glucose | Others | High-protein flour Yield (g flour/g rice) | Composition (%) Protein | Starch | Sugar |
|---|---|---|---|---|---|---|---|---|---|---|
| Tainung 70 | 11 | 0.697 | 12.8 | 79.5 | 2.2 | 5.6 | 0.303 | 30.3 | 31.3 | 22.3 |
| Taichung Glutinous 70 | 9 | 0.816 | 10.9 | 77.6 | 1.9 | 9.5 | 0.184 | 52.9 | 16.4 | 17.7 |
| Taichung Sen Glutinous | 7 | 0.766 | 14.0 | 76.5 | 2.0 | 7.6 | 0.234 | 51.4 | 24.2 | 10.7 |
| Taichung Native 1 | 9 | 0.638 | 12.8 | 80.2 | 2.6 | 4.5 | 0.362 | 28.5 | 38.7 | 13.9 |
|  | 14 | 0.720 | 15.5 | 76.4 | 3.0 | 5.1 | 0.280 | 37.7 | 23.7 | 32.5 |
|  | 4 | 0.590 | 10.5 | 84.3 | 1.5 | 3.7 | 0.410 | 25.2 | 42.0 | 12.0 |

TABLE II

High-Maltose Syrup Production from α-Amylase-thinned Rice flour (Taichung Native 1. 10% DS, DE 9) with B. cereus β-Amylase and Isoamylase at 50° C., pH 4.0.

| Reaction time (hr) | Enzymes used (U g$^{-1}$ DS) β-Amylase | Isoamylase | Pullulanase | High-maltose syrup composition (%) Maltotriose | Maltose | Glucose | Others |
|---|---|---|---|---|---|---|---|
| 2 | 300 | 2000 | 0 | 8.05 | 64.95 | 2.23 | 24.77 |
| 60 | 300 | 2000 | 0 | 10.22 | 68.32 | 2.23 | 19.23 |
| 2 | 300 | 0 | 5 | 14.73 | 66.75 | 2.19 | 16.33 |
| 60 | 300 | 0 | 5 | 12.76 | 80.14 | 2.61 | 4.49 |
| 2 | 300 | 0 | 10 | 13.77 | 71.60 | 2.10 | 12.53 |
| 60 | 300 | 0 | 10 | 12.81 | 79.48 | 2.16 | 5.55 |
| 2 | 300 | 2000 | 5 | 16.91 | 75.36 | 2.06 | 5.67 |
| 60 | 300 | 2000 | 5 | 13.38 | 83.19 | 2.21 | 1.22 |

TABLE III

Maltose Syrup Production from α-Amylase Thinned Rice Flour (10% DS, DE 9) with β-Amylase and Pullulanase at 50° C.

| Time (hr) | pH | Enzymes used (U g$^{-1}$ DS) B. cereus β-amylase | Sweet potato β-amylase | Pullulanase | Maltose syrup composition (%) Maltotriose | Maltose | Glucose | Other |
|---|---|---|---|---|---|---|---|---|
| 12 | 4 | 300 | 0 | 5 | 14.56 | 77.91 | 2.15 | 5.38 |
| 60 | 4 | 300 | 0 | 5 | 12.76 | 80.14 | 2.61 | 4.49 |
| 12 | 4 | 0 | 300 | 5 | 8.96 | 56.69 | 2.29 | 32.06 |
| 60 | 4 | 0 | 300 | 5 | 10.97 | 55.31 | 3.24 | 30.48 |
| 12 | 5 | 300 | 0 | 5 | 14.83 | 77.46 | 2.23 | 5.48 |
| 60 | 5 | 300 | 0 | 5 | 13.58 | 79.64 | 2.36 | 4.42 |
| 12 | 5 | 0 | 300 | 5 | 14.03 | 78.40 | 2.22 | 5.35 |
| 60 | 5 | 0 | 300 | 5 | 15.41 | 76.01 | 3.01 | 5.57 |
| 12 | 6 | 300 | 0 | 5 | 14.71 | 76.62 | 2.10 | 6.57 |
| 60 | 6 | 300 | 0 | 5 | 14.15 | 79.29 | 2.16 | 4.13 |
| 12 | 6 | 0 | 300 | 5 | 13.66 | 78.32 | 2.49 | 5.53 |
| 60 | 6 | 0 | 300 | 5 | 15.02 | 76.51 | 2.96 | 5.51 |

TABLE IV

The composition of Maltose syrup produced from Germinating Rice (Tainung 70)

| Germinating time (days) | shoot length (cm) | yield (g syrup/ g dry rice) | Composition (%) Maltotriose | Maltose | Glucose | Others |
|---|---|---|---|---|---|---|
| 1 | 0 | 0.72 | 14.0 | 78.4 | 4.8 | 3.2 |
| 2 | 0.19 | 0.68 | 13.5 | 75.2 | 5.2 | 8.0 |
| 3 | 0.52 | 0.66 | 15.0 | 70.5 | 4.5 | 14.0 |
| 5 | 2.30 | 0.60 | 16.4 | 62.8 | 5.6 | 15.2 |

What is claimed is:

1. An enzymatic process for producing a high-maltose syrup and a high-protein byproduct from a material that contains starch and protein, said process comprising the steps of:
    liquefying starch in said material in an autoclave using an effective amount of α-amylase to obtain a soluble starch hydrolysate and heat-coagulated protein;
    separating said heat-coagulated protein from said soluble starch hydrolysate; and
    saccharifying said soluble starch hydrolysate using an effective amount of β-amylase and debranching enzymes comprising a combination of isoamylase and pullulanase.

2. The enzymatic process as claimed in claim 1, wherein said material is selected from the group consisting of rice, germinated rice, corn, barley, wheat, legumes and sweet potato.

3. The enzymatic process as claimed in claim 1, wherein said material is rice flour.

4. The enzymatic process as claimed in claim 1, wherein said α-amylase is thermostable α-amylase.

5. The enzymatic process as claimed in claim 4, wherein said α-amylase is Bacillus licheniformis α-amylase.

6. The enzymatic process as claimed in claim 1, wherein said β-amylase is selected from the group consisting of Bacillus cereus β-amylase and sweet potato β-amylase.

7. The enzymatic process as claimed in claim 1, wherein said soluble starch hydrolysate is saccharified at a temperature between 40°–60° C. and at a pH of between about 4.0 to about 6.0.

* * * * *